US011306226B2

(12) United States Patent
Hu et al.

(10) Patent No.: US 11,306,226 B2
(45) Date of Patent: Apr. 19, 2022

(54) HOT MELT ADHESIVE COMPOSITION AND USE THEREOF

(71) Applicant: HENKEL IP & HOLDING GMBH, Duesseldorf (DE)

(72) Inventors: Yuhong Hu, Belle Mead, NJ (US); Darshak R. Desai, Edison, NJ (US); Jinyu Chen, Fanwood, NJ (US); Matthew L. Sharak, Franklin Park, NJ (US)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 15/708,543

(22) Filed: Sep. 19, 2017

(65) Prior Publication Data
US 2018/0002579 A1 Jan. 4, 2018

Related U.S. Application Data

(63) Continuation of application No. PCT/US2016/018863, filed on Feb. 22, 2016.

(60) Provisional application No. 62/135,879, filed on Mar. 20, 2015.

(51) Int. Cl.
C09J 123/14 (2006.01)
B32B 7/12 (2006.01)
B32B 27/08 (2006.01)
B32B 27/12 (2006.01)
A61L 15/58 (2006.01)
C09J 123/10 (2006.01)
B32B 5/26 (2006.01)
B32B 5/02 (2006.01)
B32B 37/08 (2006.01)
B32B 37/12 (2006.01)
C09J 5/00 (2006.01)

(52) U.S. Cl.
CPC ............ C09J 123/14 (2013.01); A61L 15/58 (2013.01); B32B 5/022 (2013.01); B32B 5/26 (2013.01); B32B 7/12 (2013.01); B32B 27/08 (2013.01); B32B 27/12 (2013.01); B32B 37/08 (2013.01); B32B 37/1207 (2013.01); C09J 5/00 (2013.01); C09J 123/10 (2013.01); B32B 2037/1215 (2013.01); B32B 2307/54 (2013.01); B32B 2307/542 (2013.01); B32B 2555/02 (2013.01); C09J 2423/10 (2013.01)

(58) Field of Classification Search
CPC .......... C09J 123/14; C09J 123/10; C09J 5/00; A61L 15/58; B32B 5/022; B32B 5/26; B32B 7/12; B32B 27/08; B32B 27/12; B32B 37/1207
See application file for complete search history.

(56) References Cited

U.S. PATENT DOCUMENTS

| | | | |
|---|---|---|---|
| 4,233,432 A | 11/1980 | Curtis, Jr. | |
| 5,171,628 A | 12/1992 | Arvedson et al. | |
| 5,256,717 A | 10/1993 | Stauffer et al. | |
| 5,331,033 A | 7/1994 | Stauffer et al. | |
| 5,397,843 A | 3/1995 | Lakshmanan et al. | |
| 6,120,487 A | 9/2000 | Ashton | |
| 6,818,093 B1* | 11/2004 | Taal | C09J 153/02 156/327 |
| 16,833,404 | 12/2004 | Quinn et al. | |
| 2012/0149827 A1* | 6/2012 | Hu | C09J 123/02 524/505 |
| 2014/0371703 A1* | 12/2014 | Davis | C09J 123/16 604/385.03 |

FOREIGN PATENT DOCUMENTS

| | | |
|---|---|---|
| JP | 2013502493 A | 1/2013 |
| JP | 201364055 A | 4/2013 |
| RU | 2488618 C2 | 7/2013 |
| WO | 970393 A1 | 3/1997 |
| WO | 2009014924 A1 | 1/2009 |
| WO | 2010109018 A1 | 9/2010 |
| WO | 2012027450 A2 | 3/2012 |
| WO | 2014130180 A1 | 8/2014 |

OTHER PUBLICATIONS

Exxon Mobil. Hot melt adhesive using new metallocene polypropylene performance polymers. Oct. 21, 2014. (Year: 2014).*
Vistamaxx. Vistamaxx propylene-based elastomers: an introduction. Exxon Mobil Chemical. (Year: 2012).*
Eastotac Hydrocarbon Resins Brochure by the Eastman Company (Aug. 1992).
Specialty Polymers for Adhesives and Sealants by the Exxon Chemical Company (Oct. 1990).
Litz, R.J., Developments in Ethylene-Based Hot Melt Adhesives, Adhesives Age 17(8):35-38 (1974).
Clark, T., Bookbinding with Adhesives (3rd ed. McGraw-Hill, UK 1994), p. 1.
Alger, M.S., Polymer Science Dictionary (Elsevier Applied Science, New York 1989), p. 115.
Lee, S.M., Dictionary of Composite Materials Technology (CRC Press, Technology & Engineering 1995), p. 43.
Young, R.J. & Lovell, P.A., Introduction to Polymers (2nd ed., Chapman & Hall, New York 1991), pp. 10-11, 292.
Handbook of Adhesives (ed. Irving Skeist, Van Nostrand Reinhold Co. 1977), pp. 495-498.

(Continued)

Primary Examiner — John E Uselding
(74) Attorney, Agent, or Firm — Sun Hee Lehmann; Steven C. Bauman

(57) ABSTRACT

The sprayable olefin-based hot melt adhesive and absorbent articles comprising the adhesive are disclosed. The sprayable olefin-based hot melt adhesive is particularly suitable for spraying at low application temperatures. The sprayable low application temperature hot melt adhesives have high green strength, excellent bond strength and aging performance. Moreover, the sprayable low application temperature hot melt adhesives allows for thin bond lines without bleed-through and burn-through risks for heat-sensitive substrates.

8 Claims, No Drawings

(56) References Cited

OTHER PUBLICATIONS

Kraus et al., Tack and Viscoelasticity of Block Copolymer Based Adhesives, J. Adhesion 10:221-36 (1979).
Eastman Chemical Brochure titled "World of Eastman Chemicals" dated Jan. 1989, Publication No. P-160F.
Eastman AQ Branched Polyesters Brochure dated Sep. 1997, Publication No. WA-62B.
Eastman Chemical Sales Brochure dated Feb. 1993, Publication No. WA-21.
Exxon Chemical Sales Brochure dated Mar. 1994.
Eastman Chemical Eastotac Hydrocarbon Resins dated Nov. 1994, Publication WA-3C.
Exxon Chemical Escorez Tackifiers Brochure dated Apr. 1992.

* cited by examiner

HOT MELT ADHESIVE COMPOSITION AND USE THEREOF

FIELD OF THE INVENTION

The present invention relates to a sprayable olefin-based hot melt adhesive and absorbent articles comprising the adhesive. The sprayable olefin-based hot melt adhesive is particularly suitable for spraying at low application temperatures.

BACKGROUND OF THE INVENTION

Hot melt adhesive has an important role in the fabrication of a wearable absorbent article, e.g., diaper, sanitary napkin, adult incontinence brief. In these applications, adhesive is applied to at least one substrate such as, for example, a film substrate, a non-woven substrate, or an elastic substrate for binding the substrate to a second similar or different substrate. Upon cooling, the adhesive hardens and adheres the substrates together.

Conventional hot melt adhesives based on rubber block copolymers and/or olefin copolymers are typically applied at temperatures above 155° C. (311° F.). Lowering the application temperature of adhesives used in the manufacture of such products to 155° C. or below would improve the thermal aging in application equipment, improve safety for equipment operator, and reduce defective products since the products contain heat sensitive substrates. Hot melt adhesives suitable for such low application temperature must have low viscosity at or below 155° C. To decrease viscosity of conventional adhesives, lower molecular weight polymers and higher levels of diluent have been used at the expense of performance of the hot melt adhesive. These approaches result in lower mechanical strength, and more importantly, less resistance to flow at elevated temperature. In another approach to decrease viscosity, adding wax or other low molecular weight crystalline component results in an adhesive that suffers from a reduction in the effective open time.

Metallocene catalyzed polypropylene copolymer based hot melt adhesives provide good adhesion for various substrates; however, such adhesives are not suitable for spraying at low application temperatures due to high viscosity of the metallocene catalyzed polypropylene copolymer. Adhesives made from amorphous poly alpha olefin (APAO) copolymers, have lower viscosity and can be sprayed at low application temperature; however, such adhesives suffer from poor green strength and long open time. Moreover, APAO-based adhesives sometimes fail to form bonds that is adequate in strength to make disposable articles.

There is a continuing need for a hot melt adhesive that can be applied at low temperature, i.e., below about 155° C., which has low viscosity and forms strong bond to various substrates. Such attributes would make the adhesives particularly well-suited for use in the manufacture of disposable articles. The invention is directed to this need.

BRIEF SUMMARY OF THE INVENTION

The invention provides sprayable low application temperature hot melt adhesives. The sprayable low application temperature hot melt adhesives have high green strength, excellent bond strength and aging performance. Moreover, the sprayable low application temperature hot melt adhesives allows for thin bond lines without bleed-through and burn through risks for heat-sensitive substrates.

In one embodiment, the sprayable low application temperature hot melt adhesive comprises:

(a) about 5 to about 40 wt % of a polypropylene-polyethylene (co) polymer having (i) a propylene content of about 70 to about 95 wt % of the (co)polymer, (ii) a polydispersity (Mw/Mn) value of less than about 3.0, (iii) a melt flow rate of about 20 to about 300 g/10 min measured at 230° C./2.16 kg, in accordance with ASTM D1238, (iv) a melting point of less than about 90° C., measured in accordance with ASTM 3418, and (v) a heat of fusion value of less than about 35 J/g measured at 10° C./min heating and cooling rate in accordance with ASTM D3418-12;

(b) about 30 to about 70 wt % of a tackifier; and (c) optionally up to about 30 wt % of a wax or a plasticizer.

The adhesive has a tan δ value of greater than about 30 at 140° C., 10 rad/s and a melt (Brookfield) viscosity of about 2,000 to about 11,000 cps at 150° C., ASTM 3236-88.

In another embodiment, the sprayable low application temperature hot melt adhesive consists essentially of:

(a) about 5 to about 40 wt % of a polypropylene-polyethylene (co) polymer having (i) a propylene content of about 70 to about 95 wt % of the (co)polymer, (ii) a polydispersity (Mw/Mn) value of less than about 3.0, (iii) a melt flow rate of about 20 to about 300 g/10 min measured at 230° C./2.16 kg in accordance with ASTM D1238, (iv) a melting point of less than about 90° C. measured in accordance with ASTM 3418, and (v) a heat of fusion value of less than about 35 J/g measured at 10° C./min heating and cooling rate in accordance with ASTM D3418-12;

(b) about 30 to about 70 wt % of a tackifier;

(c) up to about 50 wt % of an amorphous poly alpha olefin polymer; and (d) up to about 30 wt % of a wax or a plasticizer;

The adhesive has a tan δ value of greater than about 30 at 140° C., 10 rad/s and a melt (Brookfield) viscosity of about 2,000 to about 11,000 cps at 150° C., measured in accordance with ASTM 3236-88.

Another aspect of the invention is directed to an article of manufacture comprising the sprayable low application temperature hot melt adhesive described herein. The article comprises a film substrate, a non-woven substrate or an elastic substrate bonded together with the sprayable low application temperature hot melt adhesive. Articles of manufacture encompassed by the invention include wearable absorbent article, e.g., diaper, sanitary napkin, adult incontinence brief and the like.

Yet another aspect of the invention is directed to a method for bonding substrates together which comprises spraying the sprayable low application temperature hot melt adhesive composition of the invention at a temperature at or below about 155° C. to a first substrate, bringing a second substrate in contact with the adhesive composition applied to the first substrate, and cooling to form a bond.

DETAILED DESCRIPTION OF THE INVENTION

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Adhesively bonded" to a substrate wherein an adhesive is used to bond a substrate (e.g., film, elastomeric film, nonwoven) or to a second similar or dissimilar substrate.

"Aged" performance (e.g. "aged bond strength") refers to measurement taken after the sample has been stored for 2 weeks at 50° C. "Initial bond strength" performance refers to measurement taken within one day after making the sample.

"Bleed-through" describes the phenomenon of when the applied adhesive seeps outside of the applied area of the substrate before hardening.

"Burn-through" describes the phenomenon of when the substrate become defective, e.g., wrinkles or forms a hole, from the heat of the applied adhesive.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" and "consists essentially of" are used herein to limit the scope of subject matter, such as that in a claim, to the specified materials or steps and those that do not materially affect the basic and novel characteristics of the subject matter.

"Low application temperature" refers to applying an adhesive at or below 155° C.

"Polydispersity index" (PDI) refers to distribution of molecular mass in a polymer. The PDI is the ratio of weight average molecular weight (Mw) to number average molecular weight (Mn). As the polymer chains approach uniform chain length, the PDI approaches the value 1.

The present invention provides a sprayable hot melt adhesive that can be applied at 155° C. or below. This sprayable hot melt adhesive has high green strength, and excellent bond strength and aging performance upon cooling. The sprayable hot melt adhesive may be applied at thin bond lines without bleed-through and burn-through risks for heat-sensitive substrates.

The term "polymer component" as used herein, refers to a single propylene (co)polymer or a blend of different (co)polymers produced by metallocene catalysis polymerization. The (co)polymer component includes block and/or random polypropylene. The propylene (co)polymer is a propylene copolymer with at least one comonomers selected from $C_2$, $C_4$-$C_{20}$ comonomers. Preferred comonomers are ethylene, butene, hexene and octene.

The polypropylene (co)polymer has a melt flow rate of about 20 to about 300 g/10 min, preferably about 40 to about 150 g/10 min, measured at 230° C./2.16 kg ASTM D1238. It has been discovered that polypropylene (co)polymer having this set of melt flow rate balances the cohesive strength and elasticity for good bond performance, while providing flexibility for good green strength and sufficient open time.

In another embodiment, the propylene (co)polymer has a PDI value of less than about 3.0, preferably less than 2.5. Such uniform polymers are typically prepared by metallocene catalysts which impart narrow molecular weight and composition distributions and sterospecificity.

The propylene (co)polymer has a propylene content greater than about 70 wt %, preferably from about 70 to about 95 wt %, based on the (co)polymer, more preferably from about 75 to about 92 wt %, and even more preferably from about 81 to about 91 wt %. This range of propylene content in the (co)polymer lends to better adhesion onto various substrates. In addition, adhesives made from this range of propylene content in the (co)polymer can better tolerate heat and aging conditions.

In a further embodiment, the polypropylene (co)polymer has a melting point of less than about 90° C., preferably less than about 70° C., and more preferably less than about 65° C., measured in accordance with ASTM 3418.

Preferably, the metallocene catalyzed polypropylene (co)polymer has a random order, without any specific order to the polymer structure. The random polypropylene (co)polymer is described as having semi-crystalline structure, and specifically contains low crystallinity in the copolymer. The term "semi-crystalline" used for the polypropylene (co)polymer indicates that the polymer contains both crystalline and amorphous regions in the solid state. In the crystalline region, the molecular chains of the polymers are all arranged in ordered three-dimensional arrays whose structure can be fully characterized by their unit cells, the smallest structural unit used to describe a crystal. The amorphous region, in contrast, do not have ordered three-dimensional structures in the solid state. Their molecular chains are arranged in a completely random fashion in space. Semi-crystalline polypropylene (co)polymer can be easily distinguished from completely amorphous polymers by observing the presence or absence of a melting point (Tm) and the associated enthalpy or heat of fusion ($\Delta$Hm) derived from the transformation of the crystalline state to liquid state upon heating. All semi-crystalline polymers exhibit a melting point, whereas the melting point is absent for amorphous polymers. Amorphous polymers undergo a transition from a glassy solid to a rubbery elastic state in a narrow temperature range around a glass transition temperature Tg. One should not confuse the glass transition temperature Tg with the melting point Tm. Unlike the melting transition of the crystalline materials, the glass transition of amorphous polymers do not have an enthalpy change peak ($\Delta$Hm) associated with it.

The polypropylene (co)polymer has a heat of fusion value of less than about 35 J/g, preferably less than 20 J/g, and more preferably less than about 15 J/g, measured in accordance with ASTM D3418-12. Heat of fusion is defined as the change in enthalpy for the conversion of a specified amount of a solid to a liquid at constant pressure and temperature, and reported as $\Delta$Hm from the DSC measurement. Heat of fusion is directly correlated to the polymer's crystallinity. Low levels of crystallinity is desirable for the polypropylene (co)polymer of the sprayable hot melt adhesive.

The propylene (co)polymer is available from various manufactures under the trade name VERSIFY (Dow Chemical), VISTAMAXX (Exxon Mobil), TAFMER (Mitsui Petrochemical), L-MODU (Idemitsu), NOTIO (Mitsui) and the like.

The polypropylene (co)polymer content in the sprayable low application temperature hot melt adhesive ranges from about 5 to about 40 wt %, based on the total weight of the adhesive.

Surprisingly, adhesives prepared with a polypropylene having specific parameters, (i) a melt flow rate of about 20 to about 300 g/10 min measured at 230° C./2.16 kg ASTM D D1238, (ii) a polydispersity (Mw/Mn) value of less than about 3.0, (iii) a propylene content of about 70 to about 95 wt % of the (co)polymer, (iv) a melting point of less than about 90° C., measured in accordance with ASTM 3418, and (v) a heat of fusion value of less than about 35 J/g measured at 10° C./min heating and cooling rate in accordance with ASTM D3418-12; is sprayable at low application temperatures, e.g., at or below 155° C., have a high green strength, bond strength and aging performance.

The adhesive of the invention may optionally contain up to about 50 wt % of an amorphous poly alpha olefin (APAO). Amorphous poly alpha olefin have higher polydispersity index, greater than 3.0, than metallocene catalyzed (co)polymer. Amorphous poly-α-olefin polymers are random copolymers or terpolymers of $C_2$ to $C_{20}$ monomers, and specifically include, ethylene, propylene, butene, and octene, and other substantially amorphous or semi-crystalline propylene-ethylene polymers. Commercially available APAOs suitable for use in the adhesive are Rextac (Rexene LLC), Eastoflex (Eastman Corpoartion) and Vestoplast (Evonik Corporation).

The sprayable low application temperature hot melt adhesive further comprises a tackifier. Useful tackifying resins may include any compatible resin or mixtures thereof such as aliphatic petroleum hydrocarbon resins; aromatic petroleum hydrocarbon resins and the hydrogenated derivatives thereof; and alicyclic petroleum hydrocarbon resins and the hydrogenated derivatives thereof. Examples of hydrogenated aliphatic tackifiers particularly suitable include Escorez 5400 from Exxon Mobil Chemicals, Arkon P115 from Arakawa and Eastotac 130R, Regalite S1100 from Eastman Chemical, and the like. Also included are the cyclic or acyclic $C_5$ resins and aromatic modified acyclic or cyclic resins. Examples of commercially available $C_5$ resins include Wingtack extra, Wingtack ET from Cray Valley USA LLC, Piccotac 9095 from Eastman Chemical, Escorez 2203 LC from Exxon Mobil Chemicals, Luhorez A1100, A2100 from Luhua Chemical Corp. Also included are polyterpene resins; phenolic modified terpene resins and hydrogenated derivatives thereof including, for example, the resin product resulting from the condensation, in an acidic medium, of a bicyclic terpene and a phenol. Examples of commercially available rosins and rosin derivatives that could be used to practice the invention include SYLVALITE RE 110L and SYLVARES RE 115 available from Arizona Chemical; Dertocal 140 from DRT; Limed Rosin No. 1,GB-120, and Pencel C from Arakawa Chemical. Examples of commercially available phenolic modified terpene resins are Sylvares TP 2040 HM and Sylvares TP 300, both available from Arizona Chemical. Other useful tackifying resins include natural and modified rosins including, for example, as gum rosin, wood rosin, tall oil rosin, distilled rosin, hydrogenated rosin, dimerized rosin, resinates, and polymerized rosin; glycerol and pentaerythritol esters of natural and modified rosins, including, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natured terpenes, including, for example, styrene/terpene and alpha methyl styrene/terpene.

Preferred tackifiers include $C_5$ resins, petroleum distillates, hydrogenated hydrocarbons, $C_5/C_9$ resins, $C_9$ resins, polyterpenes, rosins, hydrogenated rosins, rosin esters and mixtures thereof.

In one embodiment, tackifiers are synthetic hydrocarbon resins. Included are aliphatic or cycloaliphatic hydrocarbons, aromatic hydrocarbons, aromatically modified aliphatic or cycloaliphatic hydrocarbons and mixtures thereof. Non-limiting examples include aliphatic olefin derived resins such as those available from Exxon under trade name and the ESCOREZ series, Wingtack series from Cray Valley USA LLC and Eastotac series from Eastman are also useful in the invention.

Also useful are aromatic hydrocarbon resins that are $C_9$ aromatic/aliphatic olefin-derived and available from Sartomer and Cray Valley under the trade name Norsolene and from Rutgers series of TK aromatic hydrocarbon resins. Norsolene 1100 is a low molecular weight thermoplastic hydrocarbon polymer commercially available from Cray Valley.

Alpha methyl styrene such as Kristalex F 115, 1120 and 5140 from Eastman Chemicals, Sylvares SA series from Arizona chemicals are also useful as tackifiers in the invention. Mixtures of two or more described tackifying resins may be required for some formulations.

In one embodiment, the tackifier is typically present at about 30 to about 70 wt %, more preferably from about 35 to about 65 wt %, and more preferably from about 40 to about 60 wt %, based on the total weight of the adhesive.

The sprayable low application temperature hot melt adhesive optionally comprises a wax. Useful waxes have a heat of fusion greater than 50 J/g, measured at 10° C./min heating and cooling rate in accordance with ASTM D3418-12 by DSC.

Waxes suitable for use in the sprayable, low application temperature adhesives include paraffin waxes, microcrystalline waxes, polyethylene waxes, polypropylene waxes, by-product polyethylene waxes, Fischer-Tropsch waxes, oxidized Fischer-Tropsch waxes and functionalized waxes such as hydroxy stearamide waxes and fatty amide waxes. High density low molecular weight polyethylene waxes, by-product polyethylene waxes and Fischer-Tropsch waxes are conventionally referred to in the art as synthetic high melting point waxes. Useful waxes include polyethylene and polypropylene waxes, available as LICOCENE series from Clariant, SASOL from Sasol and AC series from Honeywell.

The wax component may be present in amounts of up to about 30 wt %, based on the total weight of the sprayable low application temperature hot melt adhesive.

The sprayable, low application temperature hot melt adhesive optionally, also, comprises up to 30 wt %, based on the total weight of the sprayable low application temperature hot melt adhesive, of a plasticizer. Suitable plasticizers include polybutenes, polyisobutylene, phthalates, benzoates, adipic esters and the like. Particularly preferred plasticizers include mineral oil, aliphatic oils, olefin oligomers and low molecular weight polymers, vegetable oil, animal oils, paraffinic oil, naphthenic oil, aromatic oil, long chain partial ether ester, alkyl monoesters, epoxidized oils, dialkyl diesters, aromatic diesters, alkyl ether monoester, polybutenes and polyisobutylenes, phthalates such as di-isoundecyl phthalate (DIUP), di-iso-nonylphthalate (DINP), dioctylphthalates (DOP) and mixtures thereof.

The sprayable low application temperature hot melt adhesives of the present invention may desirably also contain at least one stabilizer and/or at least one antioxidant. These compounds are added to protect the adhesive from degradation caused by reaction with oxygen induced by for example, heat, light, or residual catalyst from the raw materials such as the tackifying resin.

Among the applicable stabilizers or antioxidants included herein are high molecular weight hindered phenols and multifunctional phenols such as sulfur and phosphorous-containing phenol. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency, and correspondingly, its reactivity; this hindrance thus providing the phenolic compound with its stabilizing properties. Representative hindered phenols include; 1,3,5-trimethyl-2, 4,6-tris-(3,5-di-tert-butyl-4-hydroxybenzyl)-benzene; pentaerythrityl tetrakis-3(3,5-di-tert-butyl-4-hydroxyphenyl)-propionate; n-octadecyl-3(3,5-di-tert-butyl-4-hydroxyphenyl)-propionate; 4,4'-methylenebis(2,6-tert-butyl-phenol); 4,4'-thiobis(6-tert-butyl-o-cresol); 2,6-di-tertbutylphenol; 6-(4-hydroxyphenoxy)-2,4-bis(n-octylthio)-1,3,5 triazine; di-n-octylthio)ethyl 3,5-di-tert-butyl-4-hydroxy-benzoate; and sorbitol hexa[3-(3,5-d i-tert-butyl-4-hydroxy-phenyl)-propionate].

Such antioxidants are commercially available from Ciba Specialty Chemicals and include IRGANOX® 565, 1010, 1076 and 1726 which are hindered phenols. These are primary antioxidants which act as radical scavengers and may be used alone or in combination with other antioxidants such as phosphite antioxidants like IRGAFOS® 168 available from Ciba Specialty Chemicals. Phosphite antioxidants are considered as secondary antioxidants, and are not generally used alone. These are primarily used as peroxide decomposers. Other available antioxidants are CYANOX® LTDP available from Cytec Industries and ETHANOX® 330 available from Albemarle Corp. Many such antioxidants are available either to be used alone or in combination with other such antioxidants. These compounds are added to the hot melts in small amounts, typically less than about 10 wt %, and have no effect on other physical properties. Other compounds that could be added that also do not affect physical properties are pigments which add color, or fluorescing agents, to mention only a couple. Additives like these are known to those skilled in the art.

Other additives conventionally used in hot melt adhesives to satisfy different properties and meet specific application requirements also may be added to the adhesive composition of this invention. Such additives include, for example, fillers, pigments, flow modifiers, dyestuffs, ionic and nonionic surfactants which may be incorporated in minor or larger amounts into the adhesive formulation, depending on the purpose.

The hot melt adhesive compositions are prepared by blending the components in a melt at a temperature above about 150 to about 180° C. to form a homogeneous blend, generally about two hours. Various methods of blending are known in the art and any method that produces a homogeneous blend may be used. The blend is then cooled and may be formed into pellets or blocks for storage or shipping. These pre-formed adhesives can then be reheated to apply onto substrates.

The particular combination of the specific polypropylene (co)polymer combined with a tackifier, and optionally wax and/or a plasticizer, forms a hot melt adhesive suitable for sprayable, low application temperature adhesive. The adhesive has a tan δ value of greater than about 30 at 140° C., 10 rad/s. A skilled artisan may measure the tan δ value in various ways.

Surprisingly, the sprayable hot melt adhesive is suitable for spraying at low application temperature while also providing high green strength, excellent bond strength and aging performance for versatile substrates. Moreover, the sprayable low application temperature hot melt adhesives allow for thin bond lines without bleed-through and burn through risks for heat-sensitive substrates.

Adhesives made with conventional polypropylene are not suitable for spraying at low application temperatures. Many conventional polypropylene (co)polymers have high molecular weight and a melt flow rates below 20 g/10 min measured at 230° C./2.16 kg, which make them unsuitable as sprayable adhesives at or below 155° C. Moreover, adhesives made with other conventional polypropylene, having low molecular weight and a melt flow rate above 300 g/10 min measured at 230° C./2.16 kg, do not have sufficient cohesive strength and elasticity to provide satisfactory bond performance. In addition, combining the two types of conventional polypropylene polymers in a single adhesive results in both high viscosity and poor bond performances.

The adhesives made from the specific polypropylene (co)polymer, having a melt flow rate of about 20 g/10 min to about 300 g/10 min measured at 230° C./2.16 kg described herein, provide high bond strength (adhesion) to nonwoven and film substrates. It has been determined that the bond strength of adhesives prepared with the polypropylene (co)polymer described herein is at least an order of magnitude higher than adhesives prepared from conventional polypropylene (co)polymer on the same substrates. In addition, adhesives made from the polypropylene (co)polymer described herein continue to exhibit superior bond strength even after the bonded laminate is exposed to aging conditions of 50° C. for two weeks. Typically, the bond strength of adhesives on substrates degrade over time under aging; however, the bond strength of the adhesives on aged laminates prepared with the polypropylene (co)polymer described herein maintain similar bond strength to that of the initially formed bond. Moreover, the adhesives prepared from the polypropylene (co)polymer described herein do not gel upon exposure to high temperatures for prolonged time, e.g., 160° C. for 72 hours.

The adhesive has a Brookfield melt viscosity of about 2,000 to about 11,000 cps at 150° C., measured with spindle #27 in accordance with ASTM 3236-88. Melt viscosity is the resistance to shear in a molten state, quantified as the quotient of shear stress divided by shear rate at any point in the flowing material. This ensures versatile application of the adhesive on to substrates by means of roll coating, painting, dry-brushing, dip coating, spraying, slot-coating, swirl spraying, printing (e.g., ink jet printing), flexographic, extrusion, atomized spraying, gravure (pattern wheel transfer), electrostatic, vapor deposition, fiberization (spraying) and/or screen printing. The viscosity range is particularly suitable for fiberization application, such as Signature, Omega, Control coat, Summit, Spiral and Melt blow application, and the like.

The tan δ value, the ratio of the loss modulus G" to storage modulus G', at 140° C. of the inventive hot melt adhesive is greater than about 30. The modulus of elasticity (G') is an indication of the stiffness of the adhesive and loss modulus (G") is an indication of flow of the adhesive, and both values can be measured conventionally in the art with a rheometer. It has been discovered that adhesives having a tan(δ) value greater than 30 at 140° C. is a good indicator for determining sprayability at 155° C. or below.

It is advantageous for an adhesive to have good green strength. Green strength measures the adhesive's ability to hold two substrates together right after being brought into contact, and measured and expressed as static peel adhesion. Typically, the adhesive is sprayed on a polymer film substrate at certain add-on level and then bonded to a nonwoven substrate with certain nip pressure. Within 15 minutes after bonding the test is carried out using a static peel method, conventionally known in the art. The static peel time of the adhesives prepared with the polypropylene (co)polymer described herein exceed 300 seconds, which is considered to be satisfactory green strength for an adhesive.

Due to the superior bond strength, aged bond strength and static peel adhesion of the inventive adhesive, the adhesive is particularly suitable for adhering a substrate, such as nonwoven, polymer films, elastic film or tissue, to another substrate. Nonwoven webs of material, such as nonwoven fabric webs, may comprise sheets of individual nonwoven component layers bonded together using mechanical, thermal, or chemical bonding processes. Nonwoven webs may be formed as flat, porous sheets made directly from individual fibers, from molten plastic, and/or plastic film. Suitable nonwoven web materials that may be useful in the present invention also include, but are not limited to spunbond, meltblown, spunmelt, solvent-spun, electrospun, carded, film fibrillated, melt-film fibrillated, air-laid, drylaid, wet-laid staple fibers, and other and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, PET and PBT, polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. Exemplary films may be elastomeric polymers. Nonlimiting examples of elastomeric polymers include homopolymers, block copolymers, random copolymers, alternating copolymers, graft copolymers, and the like. Particularly suitable polymers for use in films are polypropylene and polyethylene film. Exemplary films include DH292 and DH276 film commercially available from Clopay Corporation of Cincinnati, Ohio. Other exemplary films includeK11-815 and CEX-826 elastomer film commercially available from Tredegar Film Products of Richmond, Va. Such materials are believed to have good elasticity properties.

The adhesive is applied to a substrate while in its molten state and cooled to harden the adhesive layer. The adhesive product can be applied to a substrate by a variety of methods including coating or spraying in an amount sufficient to cause the article to adhere to another substrate. Applying minimal amounts of hot melt adhesive extends the life and reduces defect to the heat-sensitive substrates. While spraying is effective at controlling the amount sprayed onto the substrates over other methods, e.g., slot; more stringent requirements are necessary for sprayable hot melt adhesive.

In some embodiments, the nonwoven and the film substrates are no thicker than about 50 micrometers, about 60 micrometers, or about 70 micrometers. Based on the material and the thickness of the materials, the substrates are heat sensitive. Applying hot adhesive onto such substrates may damage the substrates, where the substrates are melted or deformed at the site of adhesive application. It is thus, advantageous to apply the adhesive at lower temperature. It is also advantageous to apply a thin bond line to minimize damage to the substrates; however, thin bond lines decrease bond strength of the adhesive.

The inventive low application temperature hot melt adhesives allow for thin bond lines without bleed-through and burn-through risks for heat-sensitive substrates. Due to the superior adhesion strength, minimal amounts of adhesive may be used to form bonds. Also, bleed-through problems are minimized because of fast setting of the adhesive and high green strength. Moreover, the inventive adhesive is applicable at lower temperature than conventional adhesives, and therefore, substrate burn-through and deformation risks are minimized.

The properties of the invention make it particularly suitable for use in absorbent articles such as diapers, diaper pants, baby wipes, training pants, absorbent underpants, child care pants, swimwear, and other disposable garments; feminine care products including sanitary napkins, wipes, menstrual pads, panty liners, panty shields, tampons, and tampon applicators; adult-care products including wipes, pads, containers, incontinence products, and urinary shields; clothing components; athletic and recreation products; products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads; construction and packaging supplies, industrial pads including meat pads; products for cleaning and disinfecting, wipes, covers, filters, towels, bath tissue, facial tissue, nonwoven roll goods, home-comfort products including pillows, pads, cushions, masks and body care products such as products used to cleanse or treat the skin, laboratory coats, cover-ails, and the like. The sprayable, low application temperature adhesive is also useful in bottle labeling or other applications involving plastic bonding or removable pressure sensitive adhesive applications.

In one embodiment of the invention, a disposable absorbent product is provided. The disposable absorbent product will typically comprises (1) a liquid-permeable topsheet, (2) a liquid-impermeable backsheet, which topsheet may be attached to the backsheet, (3) an absorbent structure positioned between the topsheet and the backsheet, and (4) a hot melt adhesive having the properties described herein.

Nonwovens are used commercially for a variety of applications including insulation, packaging (e.g., foods such as meat), household wipes, surgical drapes, medical dressings, and in disposable articles such as diapers, adult incontinent products and sanitary napkins. Tissue is a closely related material in which the individual fibers may or may not be chemically bonded to one another.

Exemplary of materials suitable for use as the topsheet are liquid-permeable materials, such as spunbonded polypropylene or polyethylene having a basis weight of from about 10 to about 25 grams per square meter.

Backsheets often used in disposable absorbent products are generally prepared from liquid-impermeable materials which function to contain liquids, such as water, urine, menses, or blood, within the absorbent core of the disposable absorbent product and to protect bedding and/or a wears' outer garments from diluent or a plasticizer. Materials useful as a backsheet in a disposable absorbent product are generally impermeable to liquid but are permeable to vapor. Examples are liquid-impervious materials such as polyolefin films, e.g., polypropylene and polyethylene, as well as vapor-pervious materials, such as microporous polyolefin films, sometimes referred to as breathable films.

A particularly desirable backsheet material is a film comprising a polyolefin polymer such as a linear low density polyethylene and a filler. As used herein a "filler" is meant to include particulates and other forms of materials which can be added to the film polymer extrusion blend and which will not chemically interfere with or adversely affect the extruded film but which are able to be uniformly dispersed throughout the film. When the film is stretched during processing, the filler generally causes a network of holes to be formed in the film. Such holes are generally small enough to prevent the passage of a liquid, but are generally large enough to allow vapor to pass through the holes. Generally the fillers will be in particulate form and usually will have somewhat of a spherical shape with average particle sizes in the range of about 0.1 to about 7 microns. Both organic and inorganic fillers may be used in the practice of the invention provided that they do not interfere with the film formation process. Examples of fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivatives, chitin and chitin derivatives.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

The invention will be described further in the following examples, which are included for purposes of illustration and are not intended, in any way, to be limiting of the scope of the invention.

Heat of fusion and peak melting temperature were measured with a DSC, in accordance with ASTM D3418-12.

Viscosity for polymers having a MFR greater than 1000 g/10 min 230° C./2.16 kg was measured with a Brookfield viscometer, spindle #27 at 190° C., in accordance with ASTM 3236-88.

Table 1 lists various polypropylene (co)polymers with its comonomer, polypropylene content, melt flow rate polydispersity (Mw/Mn), heat of fusion, and melting peak. For polymers having a melt flow rate greater than 1000 g/10 min at 230° C./2.16 kg, Brookfield viscosity at 190° C. was measured and reported.

TABLE 1

| Polypropylene (co)polymers | | | | | |
|---|---|---|---|---|---|
| Polymer | Comonomers/ polypropylene content | MFR g/10 min 230° C./ 2.16 kg | Poly-dispersity (Mw/Mn) | Heat of Fusion (J/g) | Melting peak (° C.) |
| P1 Vistamaxx 6502 | $C_3/C_2$ 87% | 48 | 2.03 | 12 | 60 |
| P2 Vistamaxx 2330 | $C_3/C_2$ 90% | 300 | 2.2 | 3.4 | 161 |
| P3 Vistamaxx 6202 | $C_3/C_2$ 85% | 18 | 2.08 | 3.2 | 109 |
| P4 Vistamaxx 8816 | $C_3/C_2$ 89% | >1000[a] | 4.5 | 38 | 126 |
| P5 Vistamaxx 3000 | $C_3/C_2$ 89% | 8 | 2.1 | 17.7 | 63 |
| P6 L-Modu S400 | $C_3$ 100% | >1000[b] | 2.1 | 3.5 | 78 |
| P7 L-Modu S600 | $C_3$ 100% | 500 | 2.1 | 16.7 | 76 |
| P8 Licocene 1602 | $C_3/C_2$ 90% | >1000[c] | 2.2 | 16 | 70 |
| P9 Eastoflex E1060 | $C_3/C_2$ 93% | >1000[d] | 6.6 | 0.5 | 159 |

[a] Measured Brookfield viscosity at 190° C. was 800 cps
[b] Measured Brookfield viscosity at 190° C. was 7000 cps
[c] Measured Brookfield viscosity at 190° C. was 3850 cps
[d] Measured Brookfield viscosity at 190° C. was 5550 cps Polymer 1 (P1) has the following parameters: a melt flow rate of about 20 to about 300 g/10 min measured at 230° C./2.16 kg ASTM D1238, (ii) a polydispersity (Mw/Mn) value of less than about 3.0, (iii) a propylene content of about 70 to about 92 wt % of the (co)polymer, (iv) a melting point of less than about 70° C., and (v) a heat of fusion value of less than about 20 J/g. Polymers 2-9 fall outside at least one of those parameters.

Adhesives were prepared with 20 wt % polypropylene (co)polymer as noted in Table 2 with 56.5 wt % tackifier (Wingtack Extra), 3 wt % wax (H1 wax), 20 wt % plasticizer (Nyflex 222B) and 0.5 wt % anti-oxidant (Evernox 10). The adhesive was prepared by mixing all of the components at 150 to a180° C. for about two hours.

Viscosity of the adhesive was measured using a standard Brookfield viscometer, spindle 27, at 140° C. and 150° C. in accordance with ASTM 3236-88.

A TA Dynamic Mechanical Analyzer (ARES-M LS) was used to obtain the tan δ using a temperature ramp test from Orchestrators software version 7.2.0.4. Steel parallel plates, 25 mm in diameter (316 Stainless Steel, Part # 708-00966-1 from TA instruments), and separated by a gap of about 1 mm were used for this test. The sample was loaded and then heated to 160° Cat required temperature and the temperature ramp started once equilibrium 160° C. reached. The program test data points every 10 second intervals. The convection oven (type ARES-LN2) was flushed continuously with cool nitrogen gas. The cooling rate is at 5° C./min until reaches 0° C. The convection oven was flushed continuously with nitrogen. The frequency was maintained at 10 rad/s. The initial strain at the start of the test was 50% (at the outer edge of the plates). An autostrain option in the software was used to maintain an accurately measurable torque throughout the test. The option was configured such that the maximum applied strain allowed by the software was 80%. The auto-strain program adjusted the strain at each temperature increment if warranted using the following procedure. If the torque was below $19.62 \times 10^{-3}$ Nm, the strain was decrease by 5% of the current value. If the torque was above $117.72 \times 10^{-3}$ Nm, it was decreased by 25% of the current value. At torques between 19.62×10⁻³ and 117.72×10⁻³ Nm, no change in strain was made at that temperature increment. The shear storage or elastic modulus (G') and the shear loss modulus (G") are calculated by the software from the torque and strain data. Tan δ is reported as G"/G' at 140° C., that is $$\text{Tan } \delta = G''/G' \text{(at 140° C.).}$$

TABLE 2

Adhesives

|  | Sample 1 | Comparative Sample A | Comparative Sample B | Comparative Sample C | Comparative Sample D |
|---|---|---|---|---|---|
| Polypropylene (co)polymer | P1 Vistamaxx 6502 | P3 Vistamaxx 6202 | P5 Vistamaxx 3000 | P7 LMP S600 | P8 Liccocene 1602 |
| Viscosity @ 150° C. | 4790 | 7750 | 23250 | 1495 | 330 |
| Viscosity @ 140° C. | 6975 | 11370 | 34060 | 2195 | 465 |
| Tanδ @ 140° C. | 31 | 19 | 6.5 | 63 | 65 |

Polymer 1, Comparative Samples C and D have a viscosity range that is suitable for spray application. Moreover, tan δ value of Polymer 1, Comparative Samples C and D at 140° C. is above 30, which indicates that these polymer is sprayable at 155° C. or below. Comparative Samples A and B have significantly higher viscosities and tan δ value of less than 30 at 140° C.

Each adhesive samples listed in Table 2 was applied onto DH 292 PE from Coplay Corp of Cincinnati, Ohio by spraying using a Signature applicator head from Nordson Corp at 150-155° C. at a line speed of 1000 feet per minute with adds-on 2.5 gsm. A second substrate (15 gsm nonwoven from PGI) was then applied onto the adhesive, making a bonded article.

The bond strength of nonwoven to film was measured with a tensile tester in Mode I T-peel configuration for initial and aged samples. A suitable tensile tester should provide a computer interface for universal tensile testing at constant rate, such as the Sintech 1/D Tensile Testing Machine (MTS, Model 1500 BZF-50, USA) or equivalent. The tensile machine should be fitted with a high precision 222 N load cell or equivalent. The samples tested were into a substantially rectilinear shape with a precision cutter from Thwing-Albert Instruments Co., Philadelphia, Pa. or equivalent and was sized to the sample dimensions to be tested. Sample dimensions were selected to achieve the required strain with forces appropriate for the instrument. Sample dimensions are approximately 2 inches wide by approximately 6 inches long. The length of the sample were aligned with the machine direction, that is, MD direction. The samples were equilibrated at 23° C.±2° C. for a minimum of one hour before testing at that same temperature. The fixtures and grips were installed with light duty jaws (flat face or bar lines may be used) that are appropriately sized to the sample dimensions tested. The instrument was calibrated according to the manufacturer's instructions. The distance between the lines of gripping force (gauge length) was 1 inch, which was measured with a steel ruler held beside the grips. The force reading on the instrument was zeroed to account for the mass of the fixture and grips. The samples (2 inches wide by approximately 6 inches long) were prepared for T-peel test using the following procedure:

(1) Mark the sample with a pen, making a line across the 2-inch width of the sample at a location 1 inch from the end of the sample. (2) Secure a piece of masking tape (Corporate Express, MFG# CEB1X60TN, from Paperworks, Inc at pwi-inc.com or equivalent), with 6 inches long and 2 inches wide on the entire film side; (3) Stretch the sample in small increments in the 2 in² area between the pen mark and the end of the sample to initiate delamination of the nonwoven fibers from the film. (4) Secure a piece of masking tape with 4 inches long and 1 inch wide, centered across the top 2 inches width of sample on the end of the sample which has been stretched to initiated delamination, Apply pressure to bond the tape to the sample. The tape is placed on the 2 inches wide surface opposite to the side of nonwoven. This tape will support the film portion of the t-peel sample after steps 5 and 6 are complete. (5) Carefully pull the fibers off of the film on the side of the nonwoven, in the 2 in² area between the pen mark and the end of the sample. For samples that are well bonded, this can be achieved by gently abrading the sample with a rubber eraser in the approximate direction toward the pen mark. (6) Carefully peel the nonwoven off the film to the pen mark. (7) Place a second piece of tape, 4 inches long and 1 inch wide, centered across the top 2 inches width of the nonwoven fibers that have been intentionally delaminated from the sample to form the nonwoven portion of the T-peel sample. To perform the T-peel test, mount the sample into the grips in a T-peel configuration with the nonwoven portion of the T-peel sample mounted in the bottom grip and the film portion of the T-peel sample mounted into the top grip. The specimen is mounted into the grips in a manner such that there is minimal slack and the force measured is less than about 0.02N. The crosshead moves up at a constant crosshead speed of 12 in/min and the sample is peeled until the respective materials (nonwoven fibers and film) separate completely. The force and extension data are acquired at a rate of 50 Hz during the peel. The peel force (g) during the first 8 inches of extension is reported as the Mode I bond strength.

A minimum of five samples was used to determine the average initial bond strength. The Bond Strength for initial and aged samples was determined as:

Bond Strength [g/in]=Average Peel Force [g]/specimen width [in].

The same test was conducted for aged samples, where the sample laminates were aged for 2 weeks at 50° C. The aged samples were then equilibrated at 23°±2° C. for a minimum of one hour before testing at that same temperature. Again, a minimum of five samples was used to determine the average aged bond strength. Initial and aged bond strengths of the adhesives are reported in Table 3.

Bonded samples were made to measure the static peel holding time. The static peel holding time is measured within 15 minutes of forming the bonded laminate. Sample adhesive was sprayed onto a polymer film using a Signature applicator head with 2.5 gsm add-on and 1000 feet per minute speed, then immediately covered with a nonwoven substrate with 75 psi nip pressure to form the bonded laminate. The coating width is 2 inches wide. The bonded laminates are then cut into 1 inch wide by 4 inches long. The length of the sample were aligned with the cross machine direction, that is, CD direction and 2 in² adhesive area is in the center. The static peel samples were prepared using the following procedures: The whole 4-inch long sample has 1 inch on the top and bottom respectively without adhesives which could easily be opened. Place a masking tape, 2 inches long and 1 inch wide, centered across the top 1 inch width of the nonwoven to secure the nonwoven end, and another piece of masking tape to secure the poly portion end to form a the static peel sample. The samples were tested at 23° C.±2° C. The opened 1 in² area of Poly film side of the bond is clamped onto a shear tester while a 50 gram weight is clamped onto the opened 1 in² of nonwoven portion, suspending from the nonwoven substrate. The time is recorded from the start of 50 gram weight suspension to the nonwoven totally separating from the film when the weight pulls down the nonwoven completely. This time is static peel, and five bonded specimen for each sample were tested and the average is listed in Table 3.

TABLE 3

|  | Sample 1 | Comparative Sample A | Comparative Sample B | Comparative Sample C | Comparative Sample D |
|---|---|---|---|---|---|
| Spraying temp | 154° C. | Not sprayable @ 170° C. | Not sprayable @ 170° C. | 150° C. | 150° C. |
| Initial Bond strength (g/in) | 255 | n/a | n/a | 21 | 92 |
| Aged Bond strength (g/in) | 336 | n/a | n/a | 29 | 45 |
| Static peel holding time (Green Strength) (sec) | 500 | n/a | n/a | 961 | 54 |

Samples A and B were not sprayable at 155° C. or below. Comparative Samples C and D were sprayable at 150° C.; however, bond strengths were significantly compromised. Only Sample 1 was sprayable at 155° C. or below and had adequate bond strengths and static peel value.

TABLE 4

|  | Sample 1 | Sample 2 | Comparative Sample E |
|---|---|---|---|
| Vistamaxx 6202 (P3) |  |  | 17 |
| Vistamaxx 6502 (P1) | 20 | 17 |  |
| RT 2315 |  | 10 |  |
| Eastoflex 1060 |  |  | 10 |
| Wingtack Extra | 56.5 | 49.5 | 49.5 |
| Sasol H1 wax | 3 | 3 | 3 |
| Nyflex 222B | 20 | 20 | 20 |
| Evernox 10 | 0.5 | 0.5 | 0.5 |
| Total | 100 | 100 | 100 |
| Viscosity |  |  |  |
| Viscosity @ 150° C. | 4790 | 2400 | 4200 |
| Viscosity @ 140° C. | 6975 | 3675 | 8000 |
| Tanδ @ 140° C. | 31 | 48 | 27 |
| Spraying temp | 154° C. | 150° C. | 165° C. |
| Initial Bond strength (g/in) | 255 | 189 | 168 |
| Aged Bond strength (g/in) | 336 | 346 | 328 |
| Static peel holding time (Green Strength) (sec) | 500 | 600 | 720 |

RT 2315 is a PP/PE amorphous polyalphaolefin from Rextac, Eastoflex 1060 is a PP/PE amorphous polyalphaolefin from Eastman Chemical company. Sample 1 and Sample 2 were sprayable at 155° C. or below and had adequate bond strengths and static peel value, while sample E required much higher temperature, 165° C., than Samples 1 and 2 to spray.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A hot melt adhesive comprising:
    (a) 15 to about 25 wt % of a single polymer component, and not a blend of different (co)polymers produced by metallocene catalysis polymerization, consisting of a polypropylene-polyethylene (co) polymer having (i) a propylene content of about 81 to about 91 wt % of the (co)polymer (iii) a melt flow rate of 40 to about 150 g/10 min as measured at 230° C./2.16 kg ASTM D1238, (iv) a melting point of less than about 65° C. and (v) a heat of fusion value of less than about 20 J/g;
    (b) 50 to about 60 wt % of a tackifier; and
    (c) up to about 30 wt % of a wax and a plasticizer;
    wherein the adhesive has (i) both initial and aged bond strength at 2.5 gsm add-on greater than 100 g/in, (ii) Green strength per static peel time greater than 300 seconds at 2.5 gsm add-on, (iii) a tan(o) value of greater than about 30 at 140° C., 10 rad/s, and (iv) a melt viscosity of about 2,000 to about 11,000 cps at 150° C., measured in accordance with ASTM 3236-88;
    and
    wherein the adhesive is sprayable at 140-155° C.

2. The hot melt adhesive of claim 1, wherein the tackifier is selected from the group consisting of $C_5$ resins, petroleum distillates, hydrogenated hydrocarbons, $C_5/C_9$ resins, $C_9$ resins, polyterpenes, rosins, hydrogenated rosins, rosin esters and mixtures thereof.

3. The hot melt adhesive of claim 1, wherein the wax is selected from the group consisting of paraffin, microcrystalline, polyethylene, polypropylene Fischer-Tropsch wax, oxidized Fischer-Tropsch, functionalized wax, and mixtures thereof.

4. The hot melt adhesive of claim 1, wherein the plasticizer is selected from the group consisting of polybutenes, polyisobutylene, paraffinic oil, naphthenic oil, phthalates, benzoates, adipic esters, mineral oil, aliphatic oils, aromatic oil, long chain partial ether ester, alkyl monoesters, epoxidized oils, dialkyl diesters, aromatic diesters, alkyl ether monoester and mixtures thereof.

5. An article comprising the adhesive of claim 1 interposed in between two substrates.

6. The article of claim 5, where in the substrate is selected from the group consisting of nonwoven, polymer film, elastic film, and tissue.

7. The article of claim 5, which is a diaper, training pant, absorbent underpant, sanitary napkin, medical gown, mead pad or disinfecting wipe.

8. A method of forming a bonded article comprising the steps of:
    1) spraying the hot melt adhesive compositions of claim 1 onto at least a portion of a first substrate at a temperature of about 155° C. or below at an add-on level of 0.1 to about 10 gsm;
    2) applying a second substrate on the hot melt adhesive; and
    3) cooling the hot melt adhesive composition to room temperature.

* * * * *